(12) United States Patent
Jenkins et al.

(10) Patent No.: US 11,317,834 B2
(45) Date of Patent: May 3, 2022

(54) SYSTEMS, APPARATUS, AND METHODS FOR DISCRIMINATING OPTICAL SIGNALS

(71) Applicant: Senseonics, Incorporated, Germantown, MD (US)

(72) Inventors: Bill Jenkins, Germantown, MD (US); Szymon Tankiewicz, Germantown, MD (US)

(73) Assignee: Senseonics, Incorporated, Germantown, MD (US)

( * ) Notice: Subject to any disclaimer, the term of this patent is extended or adjusted under 35 U.S.C. 154(b) by 756 days.

(21) Appl. No.: 16/103,464

(22) Filed: Aug. 14, 2018

(65) Prior Publication Data

US 2019/0046090 A1    Feb. 14, 2019

Related U.S. Application Data

(60) Provisional application No. 62/545,141, filed on Aug. 14, 2017.

(51) Int. Cl.
| | | |
|---|---|---|
| *A61B 5/145* | (2006.01) | |
| *A61B 5/1455* | (2006.01) | |
| *A61B 5/1459* | (2006.01) | |
| *A61B 5/00* | (2006.01) | |

(52) U.S. Cl.
CPC .......... *A61B 5/1451* (2013.01); *A61B 5/0031* (2013.01); *A61B 5/1455* (2013.01); *A61B 5/1459* (2013.01); *A61B 5/14532* (2013.01); *A61B 5/14546* (2013.01)

(58) Field of Classification Search
CPC ... A61B 5/1451; A61B 5/1459; A61B 5/1455; A61B 5/14546; A61B 5/14532; A61B 5/0031

USPC .......... 600/316, 310, 322, 324, 309
See application file for complete search history.

(56) References Cited

U.S. PATENT DOCUMENTS

| | | | |
|---|---|---|---|
| 5,488,567 A | 1/1996 | Allen et al. | |
| 5,488,597 A * | 1/1996 | Chen ........................ | G11B 7/24 369/100 |
| 6,330,464 B1 | 12/2001 | Colvin, Jr. et al. | |
| 6,711,423 B2 * | 3/2004 | Colvin, Jr. ........... | G01N 21/552 600/317 |
| 7,016,714 B2 * | 3/2006 | Colvin, Jr. ............ | A61B 5/076 600/316 |

(Continued)

*Primary Examiner* — Navin Natnithithadha
(74) *Attorney, Agent, or Firm* — Rothwell, Figg, Ernst & Manbeck, P.C.

(57) ABSTRACT

An analyte sensor incorporates one or more techniques for discriminating between different optical signals. In one embodiment, the sensor includes a photodetector that detects a narrow band optical signal. In another embodiment, the sensor includes a multilayer filter including an absorption filter, a reflection filter, and a transparent layer between the absorption and reflection filters. In another embodiment, the sensor employs an indicator that emits light for a period of time after an excitation source is turned off. In another embodiment, the sensor employs a first indicator that is excited by an excitation light source and a second indicator that is excited by light emitted by the first indicator. The second indicator emits light for a period after the excitation source is turned off. In another embodiment, excitation light is polarized by a first polarizer, and a second polarizer at a photodetector passes only light polarized by the first polarizer.

15 Claims, 9 Drawing Sheets

(56) References Cited

U.S. PATENT DOCUMENTS

| | | | |
|---|---|---|---|
| 7,135,342 B2 | 11/2006 | Colvin, Jr. et al. | |
| 7,289,836 B2 * | 10/2007 | Colvin, Jr. | G01N 21/77 600/316 |
| 8,233,953 B2 * | 7/2012 | Colvin, Jr. | A61B 5/076 600/316 |
| 8,649,836 B2 * | 2/2014 | Shimizu | G01N 21/77 600/316 |
| 8,853,649 B2 * | 10/2014 | Ota | A61B 5/14532 250/458.1 |
| 9,377,351 B2 * | 6/2016 | Colvin, Jr. | G02B 6/04 |
| 10,537,269 B2 * | 1/2020 | Schaefer | A61B 5/1455 |
| 10,932,703 B2 * | 3/2021 | Schaefer | A61B 5/1455 |
| 2002/0026108 A1 * | 2/2002 | Colvin, Jr. | G01N 21/552 600/316 |
| 2002/0043651 A1 | 4/2002 | Darrow et al. | |
| 2004/0176669 A1 * | 9/2004 | Colvin, Jr. | G01N 21/7703 600/316 |
| 2006/0149143 A1 * | 7/2006 | Colvin, Jr. | G01N 33/54373 600/316 |
| 2008/0108885 A1 * | 5/2008 | Colvin, Jr. | G01N 21/7703 600/317 |
| 2011/0278441 A1 | 11/2011 | Vermeulen et al. | |
| 2012/0029328 A1 * | 2/2012 | Shimizu | A61B 5/14532 600/316 |
| 2013/0037727 A1 * | 2/2013 | Maeda | G01N 21/77 250/458.1 |
| 2013/0234042 A1 * | 9/2013 | Ota | G01N 21/77 250/458.1 |
| 2013/0324819 A1 * | 12/2013 | Colvin, Jr. | G02B 6/04 600/342 |
| 2015/0219643 A1 | 8/2015 | Song et al. | |
| 2016/0015302 A1 * | 1/2016 | Schaefer | A61B 5/1455 600/310 |

* cited by examiner

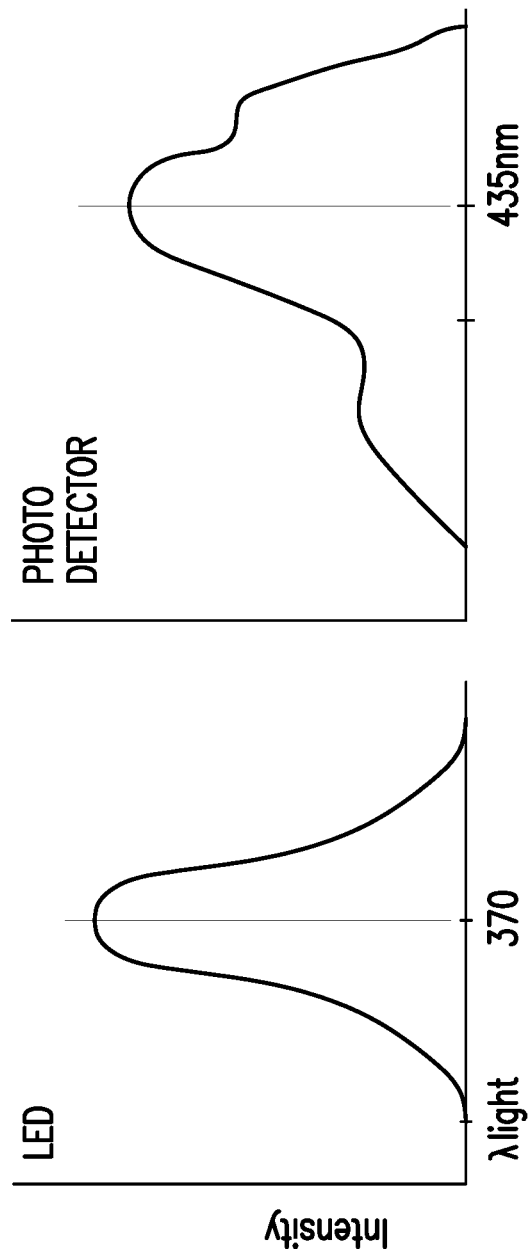

SYSTEMS, APPARATUS, AND METHODS FOR DISCRIMINATING OPTICAL SIGNALS

CROSS-REFERENCE TO RELATED APPLICATION

The present application claims the benefit of priority to U.S. Provisional Application Ser. No. 62/545,141, filed on Aug. 14, 2017, which is incorporated herein by reference in its entirety.

BACKGROUND

Field of Invention

This invention relates to analyte sensors comprising an excitation light source and an indicator that emits light when in the presence of the analyte of interest and when energized by the excitation light source and further incorporating techniques for distinguishing between excitation signals reflected from the indicator and emission signals emitted by the indicator.

Discussion of the Background

An implantable sensor for detecting an analyte of interest (e.g., glucose) may be a highly miniaturized, dual channel precision fixed fluorometer. A known configuration of such a sensor 10 is shown in FIG. 1. The sensor 10 includes an excitation light source 12 (e.g., an LED) and an indicator 14 positioned above the source 12. Indicator 14 may comprise indicator molecules embedded in a graft (i.e., layer or matrix). For example, in an implantable fluorescence-based sensor, fluorescent indicator molecules may reversibly bind glucose and, when irradiated with excitation light within a certain wavelength range (e.g., light having a wavelength of approximately 378 nm), the indicator molecules fluoresce to emit an amount of light within a wavelength range (e.g., light in the range of 400 to 500 nm) that depends on whether an analyte of interest is bound to the indicator molecule. Broadly speaking, in the context of the field of the present invention, indicator molecules are molecules for which one or more optical characteristics is or are affected by the local presence of an analyte. Sensor 10 may further include two photodetectors 16, 18 (e.g., photodiodes) arrayed symmetrically on either side of the light source 12 to receive the fluorescence for both a read channel (associated with photodiode 16) (glucose modulation) and a reference channel (associated with photodiode 18). Thus, photodetector 16 is an indicator sensor photodetector, and photodetector 18 is reference signal photodetector. The sensor 10 further includes dichroic band pass filters 20, 22 (thin film) for each channel that are coated directly onto the surface of the photodiodes 16, 18, respectively.

Exemplary sensors including a read, or indicator, channel and a reference channel are described in U.S. Pat. Nos. 6,330,464 and 7,135,342, the disclosures of which are hereby incorporated by reference.

The light source 12 of the sensor 10 emits light in an excitation wavelength range that may peak at approximately 378 nm, e.g., 358-398 nm, see FIG. 2(A), (excitation wavelength) as indicated by arrows 24 emanating from the LED 12. Much of excitation light 24 is then absorbed by indicator molecules of the indicator 14. A portion of the light emitted by the LED 12 is reflected from the indicator 14 back into the sensor 10, and some part of the absorbed LED light is emitted by fluorescing molecules of the indicator 14 at a wavelength (emission wavelength) that is at least partially different (e.g., higher) than the excitation wavelength. The reflected and emitted (fluoresced) light is absorbed by the two photodetectors 16, 18 within the body of the sensor 10.

As noted each photodetector 16, 18 is covered by a thin film filter 20, 22, respectively, that allows only a certain subset of wavelengths of light to pass through the filter and to the respective photodetector. The filters 20, 22 are thin film (dichroic) filters deposited on the glass, and they pass only a narrow band of wavelengths and otherwise reflect most light. The reference photodiode filter 22 passes light at the same wavelength as is emitted from the LED 12 (e.g., 378 nm, i.e., the excitation wavelength). The signal, or read, photodiode 16 detects the amount of fluoresced light that is emitted from the molecules in the indicator 14. In currently-available sensors, the signal filter 20 associated with the signal photodiode 16, passes light in the range of about 400 nm to 500 nm. The peak emission of the indicator 14, however, typically occurs at around 435 nm, as can be seen in the FIG. 2(B). Higher glucose levels correspond to a greater amount of fluorescence of the molecules in the indicator 14, and therefore, a greater amount of photons striking the signal photodiode and a stronger photodiode signal.

When using fluorescent detection technologies that have multiple light transmission sources (e.g., reflected excitation light as well as fluorescent emission) from the indicator a good filter design is needed to prevent light saturation of the photodiodes.

Current LED operation generates light within a small spectrum. This spectrum overlaps with the light spectrum of the indicator 14, as shown in FIGS. 2(A) and 2(B). With the current detection abilities, the LED and fluorescent emission are not independent of each other, where the reflected LED light can directly affect the fluorescent readings thereby causing inaccurate readings from the indicator emissions.

Additionally no filter design is perfect for filtering light in very narrow bands. There is always some cross talk or some light leakage causing undesirable effects and shifting data reading. FIGS. 3A and 3B demonstrate the amount of light contamination that may occur in each of the photodiodes. In FIG. 3A, filter 22 associated with reference photodetector (photodiode) 18 is configured to pass excitation light having a wavelength of approximately 370-378 nm (i.e., reflected excitation light from the LED 12) to the reference signal photodetector 18. As shown, however, a portion (e.g., 5-30%) of the fluorescent indicator emission centered at 435 nm will pass through the filter 22 to the photodetector 18. Thus, the light intensity detected by detector 18 is not due solely to the reflected excitation light. In FIG. 3B, filter 20 associated with read (signal indicator) photodetector (photodiode) 16 is configured to pass excitation light having a wavelength of approximately 435 nm (i.e., fluorescent emission from the indicator 14) to the photodetector 16. As shown, however, a portion (e.g., 10-50%) of the reflected excitation light centered at about 370 nm may pass through the filter 20 to the photodetector 16. Thus, the light intensity detected by detector 16 is not due solely to the fluorescent emission of the indicator 14.

The silicon photodiodes that are currently available have a large range (300 nm-1200 nm). These photodiodes are not ideal in the situation where both the LED and the fluorescence from the indicator molecules possess wavelengths at the lower end of this spectrum; for example, 378 nm and 435 nm, respectively.

FIG. 4 shows another illustration of the cross absorption of excitation (LED) and indicator wavelengths in adjacentlypositioned photodetectors in which inadequate filtering results in significant cross-talk between the photodetectors and in which the reference signal is too similar to the indicator signal to allow for compensation.

SUMMARY OF THE INVENTION

The present invention overcomes the disadvantages of prior systems by providing, among other advantages, improved discrimination between different optical signals Aspects of the invention are embodied in an analyte sensor comprising an indicator configured to emit light within an indicator wavelength range when in the presence of an analyte of interest and when energized by an excitation light source emitting light within an excitation wavelength range that is at least partially different from the indicator wavelength range, an excitation light source configured to emit light within the excitation wavelength range, and an indicator signal photodetector positioned to receive light emitted by the indicator and configured to detect light only within a prescribed wavelength range that includes at least part of the indicator wavelength range and does not include the excitation wavelength range.

Further aspects of the invention are embodied in an analyte sensor comprising an indicator configured to emit light within an indicator wavelength range when in the presence of an analyte of interest and when energized by an excitation light source emitting light within an excitation wavelength range that is at least partially different from the indicator wavelength range, an excitation light source configured to emit light within the excitation wavelength range, an indicator signal photodetector positioned to receive light emitted by the indicator, and an indicator signal filter constructed and arranged to transmit light only within a prescribed wavelength range to the indicator signal photodetector. The prescribed wavelength range includes at least part of the indicator wavelength range and does not include the excitation wavelength range, and the indicator signal filter comprises a first layer comprising an absorption filter, a second layer comprising a reflective filter; and a third layer comprising a transparent material disposed between the first layer and the second layer.

Further aspects of the invention are embodied in an analyte sensor comprising an indicator configured to emit light within an indicator wavelength range when in the presence of an analyte of interest and when energized by an excitation light source emitting light within an excitation wavelength range, an excitation light source configured to emit light within the excitation wavelength range, and an indicator signal photodetector positioned to receive light emitted by the indicator wherein the indicator is configured to continue to emit light for a period of time after the excitation light source stops emitting light.

Further aspects of the invention are embodied in an analyte sensor comprising a first indicator configured to emit light within a first indicator wavelength range when in the presence of an analyte of interest and when energized by an excitation light source emitting light within an excitation wavelength range, an excitation light source configured to emit light within the excitation wavelength range, a second indicator positioned to receive light emitted by the first indicator and configured to emit light within a second indicator wavelength range when energized by light emitted by the first indicator, and an indicator signal photodetector positioned to receive light emitted by the second indicator. The second indicator is configured to continue to emit light for a period of time after the excitation light source stops emitting light.

Further aspects of the invention are embodied in an analyte sensor comprising an indicator configured to emit light within an indicator wavelength range when in the presence of an analyte of interest and when energized by an excitation light source emitting light within an excitation wavelength range, an excitation light source configured to emit light within the excitation wavelength range, a first polarizer operatively associated with the excitation light source and configured to polarize light emitted by the excitation light source and to transmit polarized excitation light, an indicator signal photodetector positioned to receive light emitted by the indicator, and a second polarizer operatively associated with the indicator signal photodetector and configured to block light from the indicator signal photodetector that does not match the first polarizer.

Further variations encompassed within the systems and methods are described in the detailed description of the invention below.

BRIEF DESCRIPTION OF THE DRAWINGS

The accompanying drawings, which are incorporated herein and form part of the specification, illustrate various, non-limiting embodiments of the present invention. In the drawings, like reference numbers indicate identical or functionally similar elements.

FIGS. 2A and 2B show intensity versus wavelength plots for an LED and a photodetector, respectively.

DETAILED DESCRIPTION OF THE INVENTION

Figure 1:
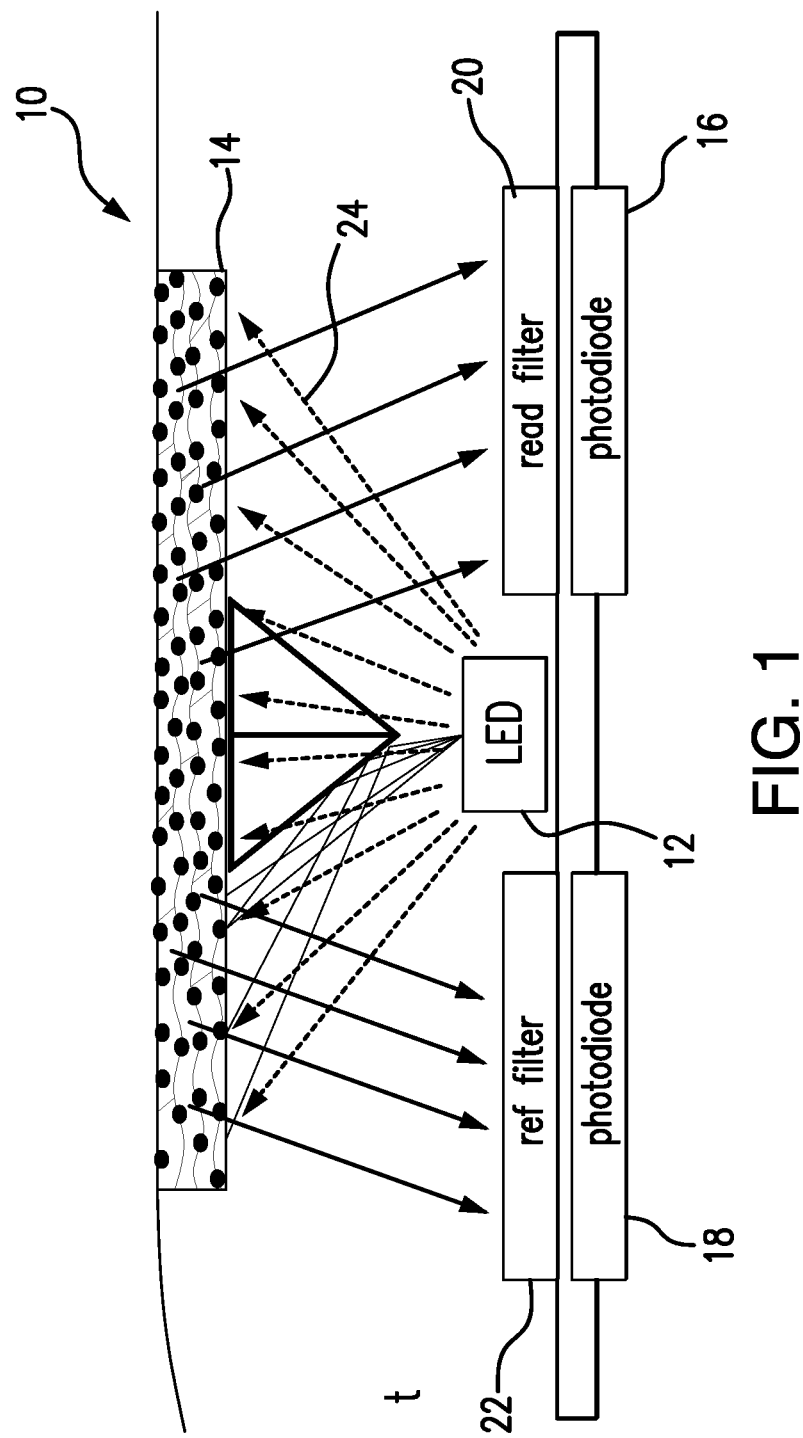
FIG. 1 shows a conventional, two-channel analyte sensor.
Figure 3A:
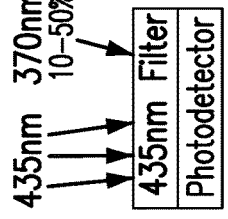
FIGS. 3A and 3B are schematic views of a photodetector with a filter positioned thereon showing the amount of light at various wavelengths passing through the filter.
Figure 3B:
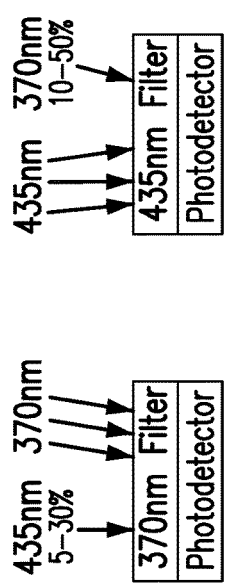
Figure 4:
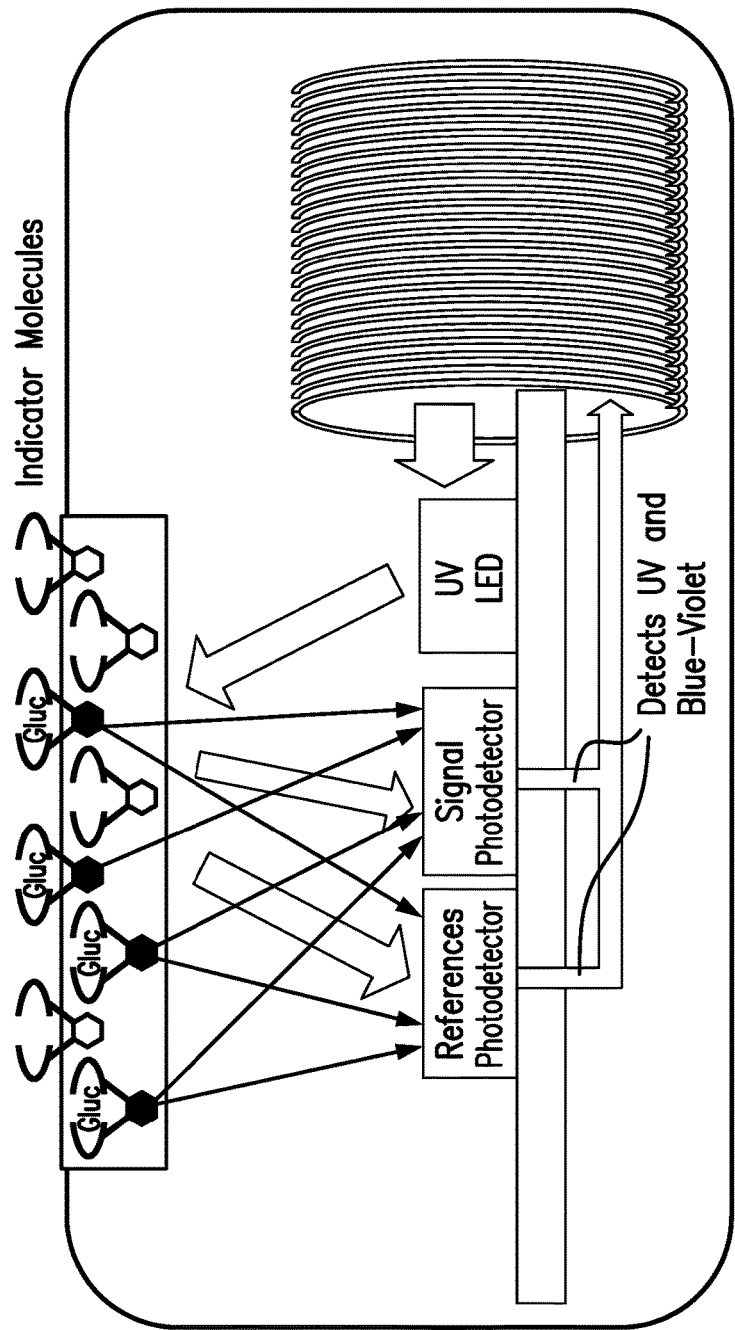
FIG. 4 is a schematic view of an alternative, conventional two-channel analyte sensor.
Figure 5:
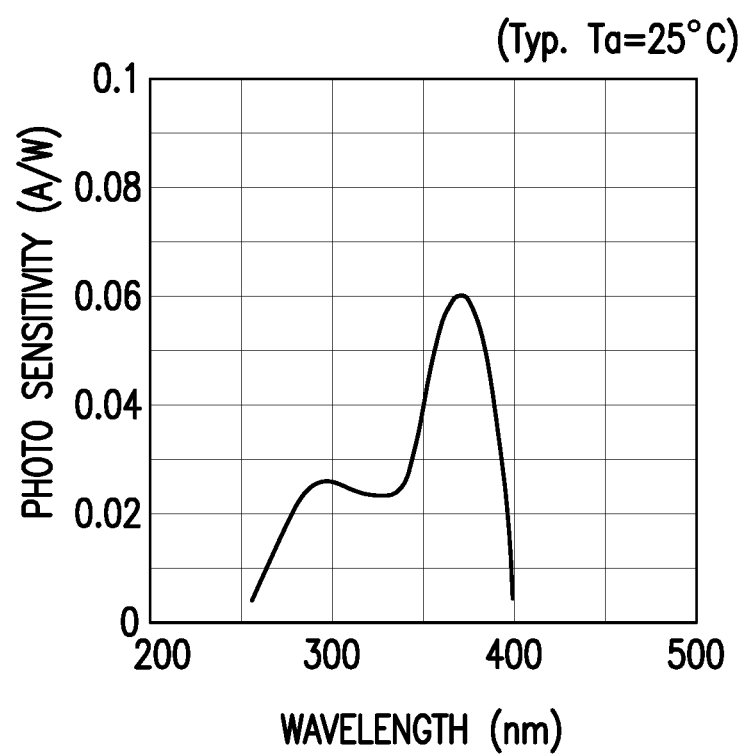
FIG. 5 is a plot of photosensitivity versus wavelength for a photodetector according to an aspect of the present invention.

According to one non-limiting embodiment of the invention, an analyte sensor may include a narrow band photodetector (e.g., photodiode) that is centered at or near the wavelength of interest. For example, for fluorescent emission centered around (for example and without limitation) 435 nm, an indicator photodetector (e.g., photodiode) may be configured to absorb light at a low wavelength bound (e.g., 420 nm) and drop off to zero at an upper wavelength bound (e.g., around 465 nm). These upper and lower ranges are exemplary, and different ranges may be selected for different applications. With a narrow range photodiode, the system will be more selective with respect to light sources. Thus, the indicator signal photodetector may be configured to detect light within a wavelength that encompasses the indicator wavelength range but does not encompass the excitation wavelength range. FIG. 5 shows an intensity vs. wavelength trace for a photodiode with a narrow wavelength range in accordance with one non-limiting embodiment of the present invention.

Similarly, for excitation light (e.g., from an LED) centered around 370-378 nm, a reference signal photodetector (e.g., photodiode) may be configured to absorb light within a range of, for example and without limitation, 350 nm to 390 nm. These upper and lower ranges are exemplary, and different ranges may be selected for different applications. Thus, the reference signal photodetector is configured to detect light within a wavelength that encompasses the excitation wavelength range but does not encompass the indicator wavelength range.

Figure 6A:
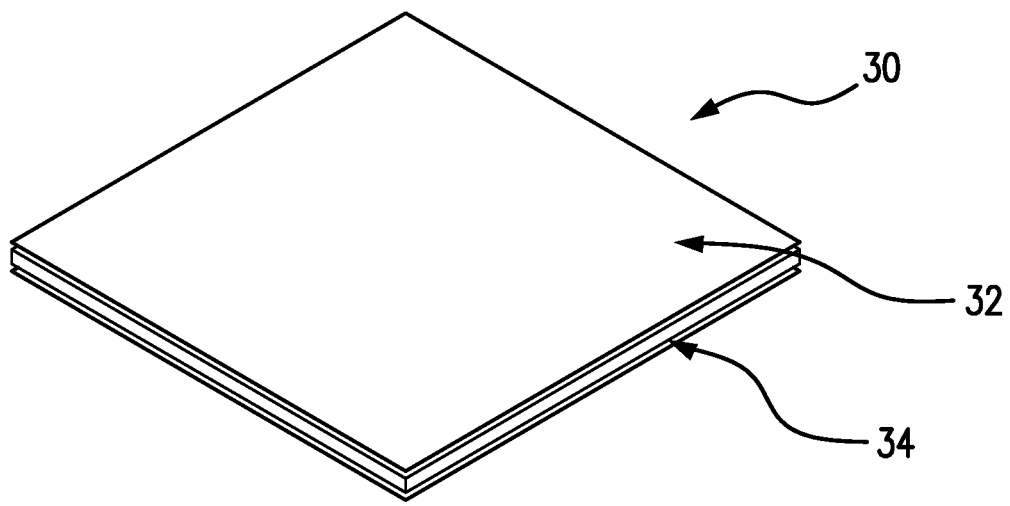
FIGS. 6A-6C show a top perspective view, an edge view, and a bottom perspective view, respectively, of a multilayer filter embodying aspects of the invention.
Figure 6B:
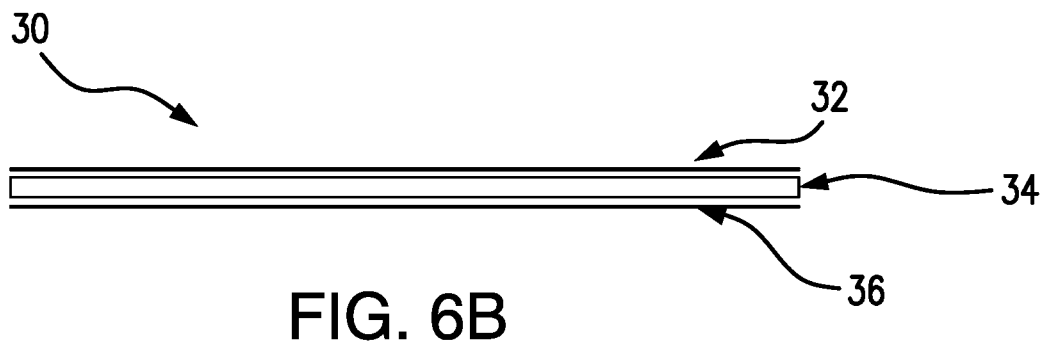
Figure 6C:
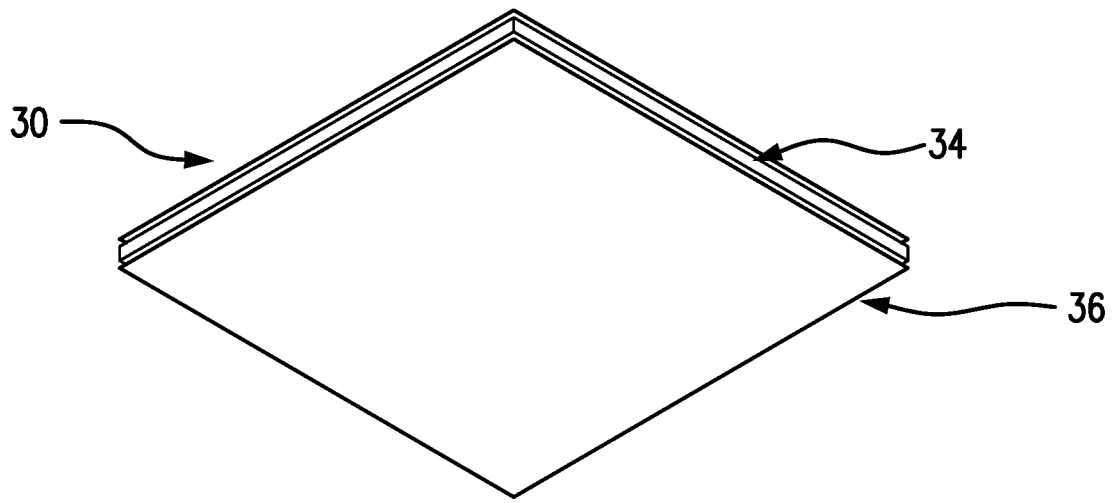

As illustrated in FIGS. 6A-6C, an analyte sensor according to a second embodiment of the invention may include a multilayer, stacked filter 30. In some embodiments, the stacked filter 30 may include an absorption filter 32, a reflective filter 36, and a transparent layer 34 (e.g., glass) sandwiched between the absorption filter 32 and the reflective filter 36. In some non-limiting embodiments, the stacked filter 30 may be operatively associated with the indicator signal photodetector and/or the reference signal photodetector.

Figure 7B:
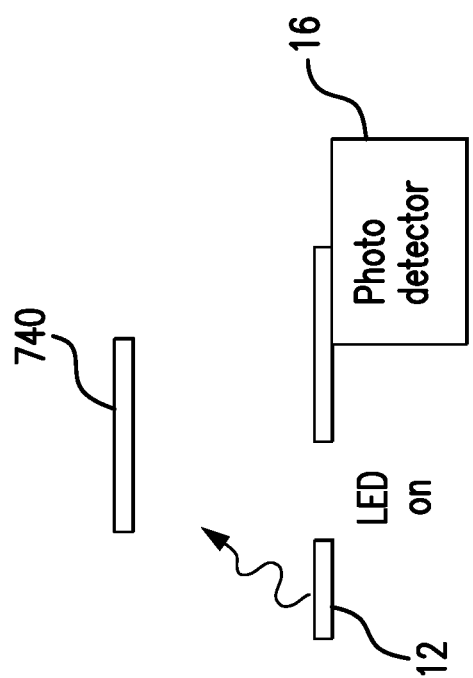
FIGS. 7A and 7B are schematic views of an analyte sensor embodying aspects of the invention and including a long illumination fluorophore indicator at first and second times, respectively.
Figure 7A:
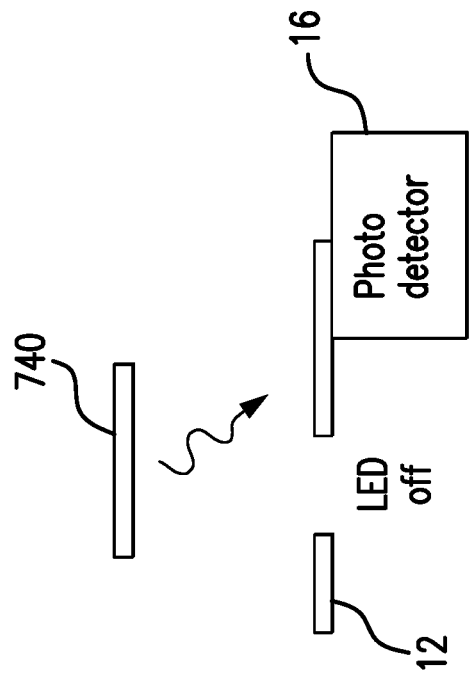

As illustrated in FIGS. 7A and 7B, an analyte sensor according to a third embodiment of the invention may include a long illumination indicator 740. In some embodiments, the long illumination indicator 740 may be, for example and without limitation, a fluorescent indicator. In some embodiments, the long illumination indicator 740 may be configured to have an emission lifetime (approx. 0.5 ms to 10 ms) that is longer than indicators presently employed in implantable glucose sensors. As shown in FIG. 7A, at time=0 seconds, the fluorophore of the indicator 740 is energized (excited) by turning on the LED light. As shown in FIG. 7B, at a later time, e.g., 1 millisecond after the LED is switched off, the fluorophore continues to fluoresce. This longer illumination by the indicator 140 will reduce data contamination because fluorescent readings may be made by the photodetector 16 after the LED is off, thereby avoiding the detection of any reflected LED light.

Although not shown in FIGS. 7A and 7B, in some embodiments, the analyte sensor may include dichroic filters operatively associated with the photodetector(s).

Figure 8A:
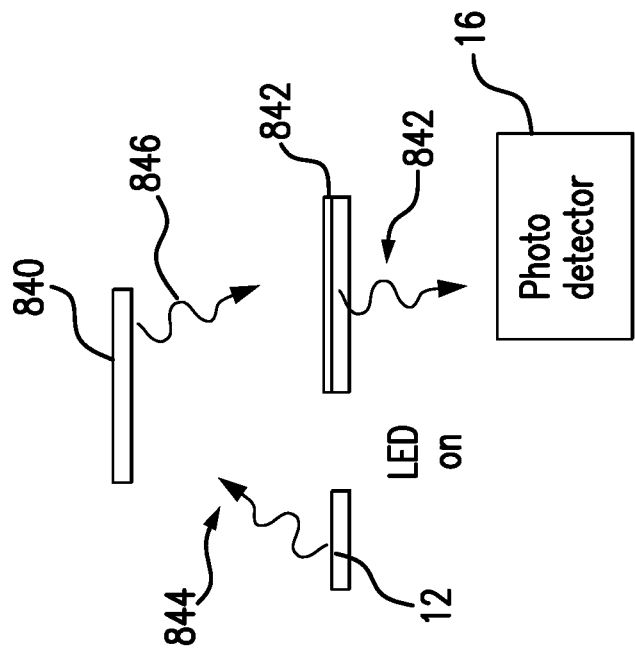
FIGS. 8A and 8B are schematic views of an analyte sensor according to an aspect of the invention and including a first indicator and a second, long illumination indicator.
Figure 8B:
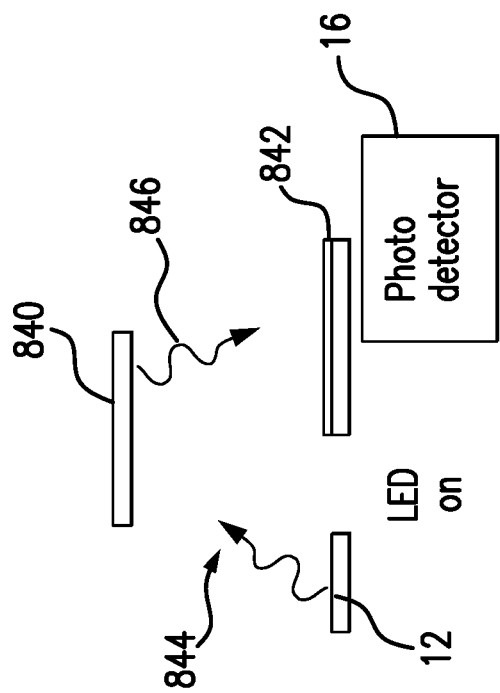

As illustrated in FIGS. 8A and 8B, to increase absorption efficiency, an analyte sensor according to a fourth embodiment of the invention may include an energy transfer system including first and second indicators 840 and 842. In some embodiments, the excitation light source 12 may emit excitation light 844 (e.g., ultraviolet (UV) light) to the first indicator 840 (e.g., a first fluorophore). In some embodiments, as shown in FIG. 8A, at time=0 seconds, the excitation light source 12 (e.g., LED) is turned on to excite the first indicator 840 (e.g., first fluorophore) with excitation light 844 (e.g., UV light (i.e., light in the wavelength range 10 nm-400 nm)). In some non-limiting embodiments, the first indicator 840 may absorb light in an excitation wavelength range, fluoresce, and emit second light 846 in a second wavelength range to the second indicator 842 (e.g., a second fluorophore). In some embodiments, the second indicator 842 may absorb light in the second wavelength range, fluoresce, and emit third light 848 in a third wavelength range. In some embodiments, the photodetector 16 may detect the third light 848 emitted by the second indicator 842. In some non-limiting embodiments, the second indicator 842 may be grafted to a glass slide above the photodetector 16. In some non-limiting embodiments, the second indicator 848 may have a long fluorescent lifetime relative to the fluorescent lifetime of the first indicator 840. In some embodiments, as shown in FIG. 8B, at a later time (e.g., 1 millisecond), after the LED is switched off, the second indicator 842 emits second light 848 that is transmitted to the photodetector 16, and, as with the system shown in FIGS. 7A and 7B, fluorescent readings may be made by the photodetector 16 after the LED 12 is off, thereby avoiding the detection of any reflected LED light. In some non-limiting embodiments, the second wavelength (e.g., 435 nm) of the second light 846 may be longer than the excitation wavelength (e.g., 378 nm) of the excitation light 844. In some non-limiting embodiments, the third wavelength (e.g., 600 nm) of the third light 848 may be longer than the second wavelength of the second light 846.

Figure 9:
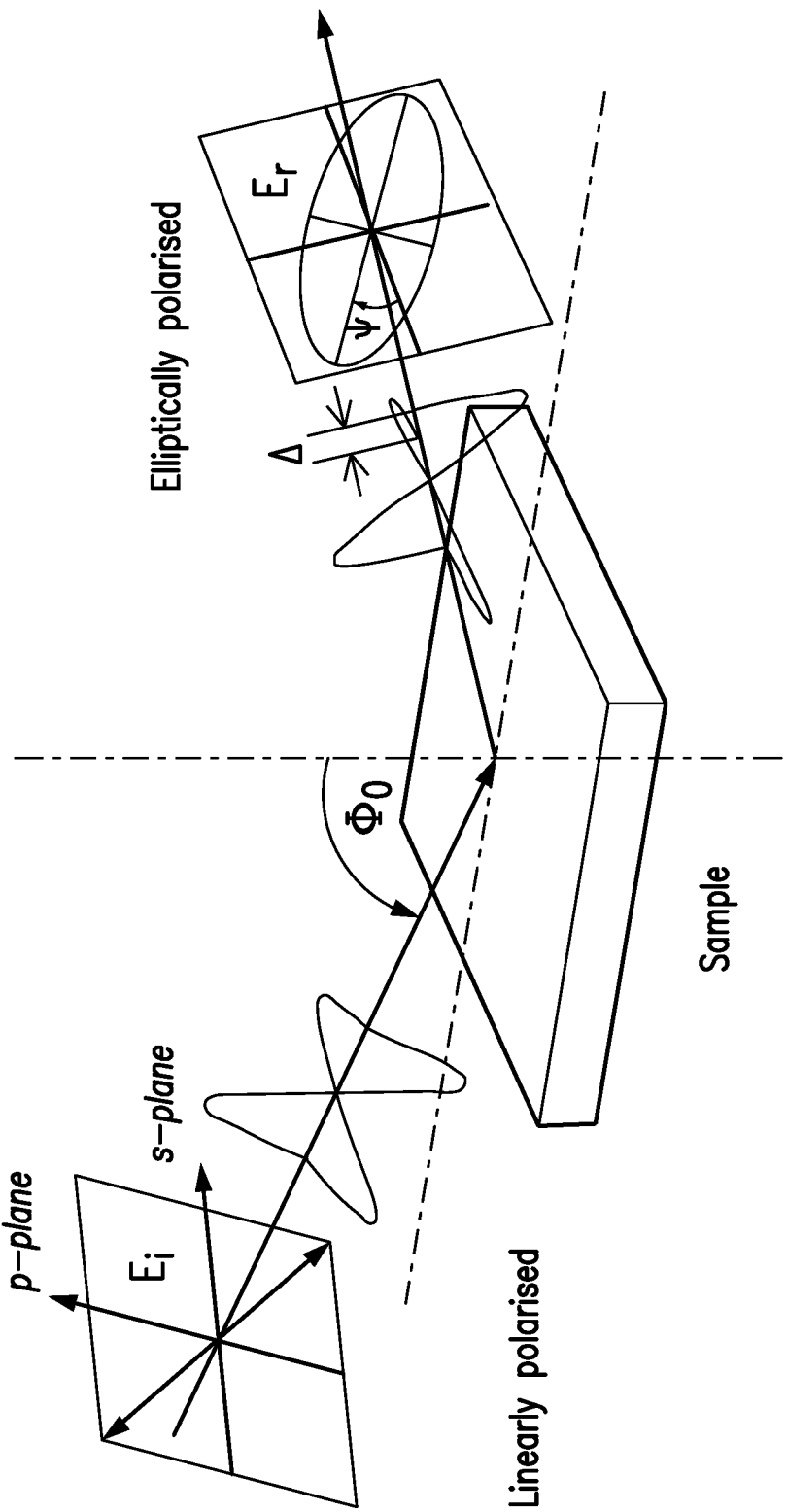
FIG. 9 illustrates optical polarization.
Figure 10:
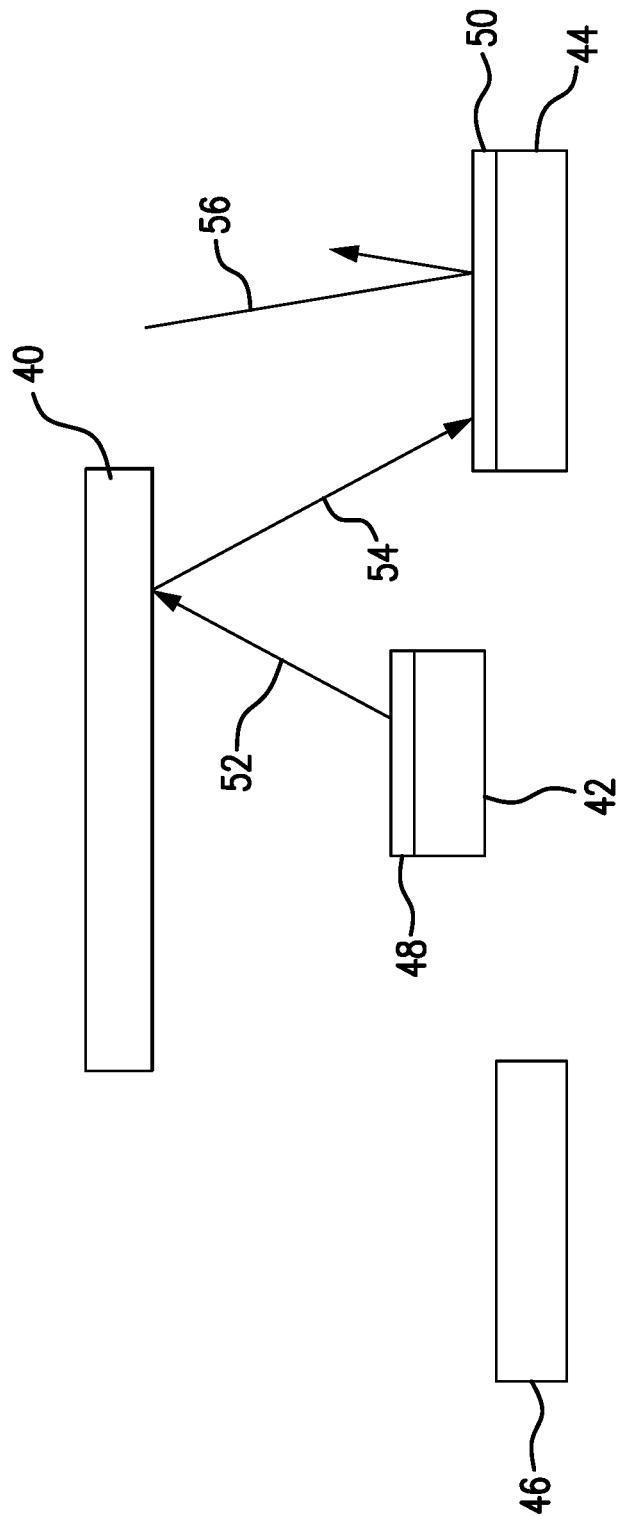
FIG. 10 is a schematic view of an analyte sensor according to an aspect of the invention and including a first polarizer associated with an excitation light source and a second polarizer associated with an indicator signal photodetector.

According to a fifth embodiment of the invention, as shown in FIGS. 9 and 10, polarized thin films may be employed to reduce or eliminate crosstalk. As illustrated in FIG. 10, a polarizer 48 (e.g., horizontal) may be placed onto the excitation source 42 (e.g., LED) to orient the UV light 52 emitted by the LED in a corresponding manner (e.g., horizontally). Orienting the LED light in this way can enhance the ability to separate the light sources at the photodetector 44 because the light 54 emitted from the indicator 40 may also be polarized. Using a second polarizer 50 placed onto the indicator signal photodetector 44, only fluorescence that is polarized in the same manner that the LED light 52 was polarized will be transmitted to the indicator signal photodetector 44 and captured for measurement.

If the orientation of light 56 does not match the polarizer 50, then the polarizer 50 blocks that light 56 from the photodetector 44.

Any two or more of the techniques described above may be combined.

Embodiments of the present invention have been fully described above with reference to the drawing figures. Although the invention has been described based upon these preferred embodiments, it would be apparent to those of skill in the art that certain modifications, variations, and alternative constructions could be made to the described embodiments within the spirit and scope of the invention.

The invention claimed is:
1. An analyte sensor comprising:
an excitation light source configured to emit light within an excitation wavelength range;
a first indicator configured to emit first light within a first indicator wavelength range when in the presence of an analyte of interest and when energized by light within the excitation wavelength range;
a second indicator configured to emit second light with a second indicator wavelength range when energized by the first light within the first indicator wavelength range; and
an indicator signal photodetector positioned to receive the second light emitted by the second indicator;
wherein the indicator signal photodetector is configured to make a second light reading during a period of time after the excitation light source stops emitting light.

2. The analyte sensor of claim 1, wherein the period of time is 0.3 msec to 10 msec.

3. The analyte sensor of claim 1, wherein the second indicator comprises a fluorophore.

4. An analyte sensor comprising:
   an excitation light source configured to emit light within an excitation wavelength range;
   a first indicator configured to emit light within a first indicator wavelength range when in the presence of an analyte of interest and when energized by light within the excitation wavelength range;
   a second indicator positioned to receive light emitted by the first indicator and configured to emit light within a second indicator wavelength range when energized by light emitted by the first indicator; and
   an indicator signal photodetector positioned to receive light emitted by the second indicator,
   wherein the second indicator is configured to continue to emit light for a period of time after the excitation light source stops emitting light.

5. The analyte sensor of claim 4, wherein the period of time is 0.3 msec to 10 msec.

6. The analyte sensor of claim 4, wherein the first indicator and the second indicator each comprises a fluorophore.

7. The analyte sensor of claim 4, wherein the first indicator wavelength range encompasses 435 nm.

8. The analyte sensor of claim 4, wherein the excitation wavelength range is 10 nm to 400 nm.

9. The analyte sensor of claim 4, wherein the second indicator wavelength range encompasses 600 nm.

10. A method comprising:
    using an excitation light source of an analyte sensor to emit excitation light within an excitation wavelength range;
    using a first indicator of the analyte sensor to emit first light within a first indicator wavelength range when in the presence of an analyte of interest and when energized by the excitation light within the excitation wavelength range;
    using a second indicator of the analyte sensor to receive the first light emitted by the first indicator and to emit second light within a second indicator wavelength range when energized by the first light emitted by the first indicator;
    using the excitation light source to stop emitting the excitation light, wherein the second indicator continues to emit the second light for a period of time after the excitation light source stops emitting the excitation light; and
    during the period of time after the excitation light source stops emitting the excitation light, using an indicator signal photodetector of the analyte sensor to receive the second light emitted by the second indicator and make a second light reading.

11. The method of claim 10, wherein the period of time is 0.3 msec to 10 msec.

12. The method of claim 10, wherein the second indicator comprises a fluorophore.

13. The method of claim 10, wherein the first indicator wavelength range encompasses 435 nm.

14. The method of claim 10, wherein the excitation wavelength range is 10 nm to 400 nm.

15. The method of claim 10, wherein the second indicator wavelength range encompasses 600 nm.

* * * * *